United States Patent [19]

Fayter, Jr. et al.

[11] Patent Number: 4,556,409
[45] Date of Patent: Dec. 3, 1985

[54] 2-VINYL- AND 2-ETHYLCYCLOPROPANE MONOCARBOXYLATES AS PLANT GROWTH MODIFIERS

[75] Inventors: Richard G. Fayter, Jr., Fairfield; Allen L. Hall, Amelia, both of Ohio

[73] Assignee: Emery Industries Inc., Cincinnati, Ohio

[21] Appl. No.: 529,317

[22] Filed: Sep. 6, 1983

Related U.S. Application Data

[62] Division of Ser. No. 333,213, Dec. 21, 1981, Pat. No. 4,418,202.

[51] Int. Cl.⁴ ............... A45C 13/10; E05B 65/52
[52] U.S. Cl. .................................. 71/76; 71/105; 71/106; 71/88; 71/90; 71/95; 71/92
[58] Field of Search ................... 71/76, 105, 106

[56] References Cited

U.S. PATENT DOCUMENTS 3,328,156 6/1967 Hopkins ........................ 71/118
3,846,112 11/1974 Fancher ......................... 71/76

Primary Examiner—Glennon H. Hollrah
Assistant Examiner—Raymond Covington
Attorney, Agent, or Firm—Kenneth D. Tremain; Gerald A. Baracka

[57] ABSTRACT

Novel 2-vinyl(or ethyl)-1-cyanocyclopropane-1-carboxylates and 2-vinyl(or ethyl)-1-arylcyclopropane-1-carboxylates useful as herbicides, pesticides and chemical intermediates are provided. The invention also relates to a method of modifying plant growth by the application of vinyl(or ethyl)cyclopropane derivatives wherein the carboxylate group contains an amine or quaternized amine moiety.

4 Claims, No Drawings

2-VINYL- AND 2-ETHYLCYCLOPROPANE MONOCARBOXYLATES AS PLANT GROWTH MODIFIERS

This application is a division of application Ser. No. 333,213, filed Dec. 21, 1981, now U.S. Pat. No. 4,418,202.

BACKGROUND OF THE INVENTION

1. Field of the Invention

The present invention is directed to novel cyclopropane compounds and, more specifically, to 2-vinyl- and 2-ethylcyclopropane compounds having a carboxylate moiety and a nitrile or aryl group substituted at the 1-position on the ring. The compounds of this invention are useful as chemical intermediates, pesticides and insecticides.

2. Discussion of the Prior Art

Pyrethrin and various synthetic compounds modeled thereafter, such as allethrin, are well known and while primarily recognized for their insecticidal properties are also useful for a variety of other applications. In view of the diverse physical and chemical properties possible with such products, much effort has been directed to the synthesis of other structurally related compounds, i.e., based on the cyclopropane structure.

The number of cyclopropane monocarboxylate compounds reported having only two of the ring positions substituted is limited and compounds of this type wherein a nitrile or aryl group is present at the same ring position as the carboxylate group are even more limited. Kierstead et al. (J. Chem. Soc., 1953, 1799–1803) reported the preparation of ethyl 1-cyano-2-vinylcyclopropane-1-carboxylate by the condensation of ethyl sodiocyanoacetate with 1,4-dibromobutene-2. The ability to obtain other related compounds was restricted, however, due to the limitations of the condensation reaction.

In U.S. Pat. No. 4,220,591 insecticidal cyclopropane esters are prepared via a carbene insertion reaction with a phenyl acrylic acid. The products conform to the formula

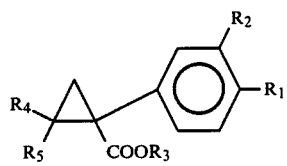

wherein $R_1$ is hydrogen or a methoxy, ethoxy, propoxy, methylthio, ethylthio, propylthio, fluoro, chloro, bromo, methyl, ethyl, nitro or amino group, and $R_2$ is a hydrogen or methyl group or $R_1$ and $R_2$ together form a methylenedioxy group; $R_3$ is hydrogen, or a lower alkyl group, or one of the following groups (a) to (d):

(a) m-phenoxybenzyl
(b) 2-benzyl-4-furylmethyl
(c) α-cyano-m-phenoxybenzyl
(c) 3,4-methylenedioxy-benzyl, and $R_4$ and $R_5$ are the same or different groups and each is a fluoro, bromo, chloro or methyl group.

SUMMARY OF THE INVENTION

Novel 2-vinyl(or ethyl)cyclopropane monocarboxylate compounds useful as pesticides, herbicides and chemical intermediates and having the 1-position substituted with a carboxylate moiety and cyano or aryl group have been prepared. The cyclopropane compounds of this invention correspond to the general formula

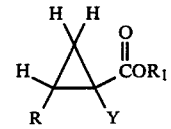

where R represents an ethyl or vinyl group, Y is selected from the group consisting of nitrile or aryl, and $R_1$ represents hydrogen, a hydrocarbon radical of an aliphatic, cycloaliphatic or aromatic group containing one or more oxygen, sulfur, nitrogen or halogen atoms; with the proviso that when Y is nitrile $R_1$ cannot be hydrogen or an alkyl group having fewer than 5 carbon atoms. $R_1$ can contain from 1 to 30 carbon atoms. Preferably $R_1$ will be an aliphatic, cycloaliphatic or aromatic hydrocarbon radical having from 1 to 20 carbon atoms or a heteroalkyl or heterocyclic radical having from 2 to 20 carbon atoms and one or more oxygen, sulfur, or nitrogen atoms in the ring system.

Especially useful cyclopropane derivatives of this invention, which have utility as plant growth modifiers, are those compounds where R is vinyl or ethyl, Y is cyano or phenyl and $R_1$ is

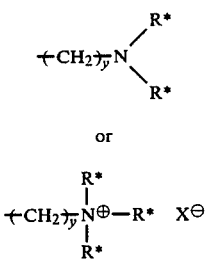

wherein R* is methyl, ethyl, hydroxymethyl or hydroxyethyl, X is chloride, bromide, hydroxide, sulfate or ethasulfate and y is an integer from 2 to 4. This invention also relates to a method of modifying the growth of plants by the application thereto of the aforementioned cyclopropane derivatives wherein the carboxylate group contains an amine or quaternized amine moiety.

Another group of especially useful cyclopropane derivatives of this invention, in view of their utility in pesticidal applications are those compounds wherein R is vinyl or ethyl, Y is cyano or phenyl and $R_1$ is 3-phenoxybenzyl, α-cyano-3-phenoxybenzyl, (5-benzyl-3-furyl)methyl and (2-benzyl-4-furyl)methyl.

DETAILED DESCRIPTION

The novel cyclopropane monocarboxylate compounds of this invention correspond to the general formula

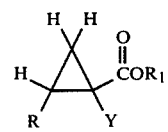

where R represents an ethyl or vinyl group, $R_1$ represents hydrogen, a hydrocarbon radical or an aliphatic, cycloaliphatic or aromatic moiety containing one or more oxygen, sulfur, nitrogen or halogen atoms and Y is selected from the group consisting of nitrile or aryl with the proviso that when Y is nitrile, R$_1$ cannot be hydrogen and if R$_1$ is alkyl the alkyl group contains 5 or more carbon atoms.

Hydrocarbon radicals from which R$_1$ is selected can contain from 1 to 30 carbon atoms and may be aliphatic, cycloaliphatic, aromatic or a combination of such moieties. When R$_1$ is an alkyl group, i.e. an aliphatic hydrocarbon radical, it will contain from 1 to 30 carbon atoms and may be straight-chain or branched, saturated or unsaturated. Especially useful radicals have from 1 to 20 carbon atoms with no more than one double bond for every four carbon atoms. Cycloaliphatic hydrocarbon radicals from which R$_1$ may be selected are saturated or unsaturated and can contain one or more hydrocarbon substituents on the ring. The cycloaliphatic radicals will have from 3 to 30 carbon atoms. Preferred cycloaliphatic radicals contain from 5 to 20 carbon atoms and correspond to the formula

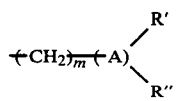

where m is an integer from 0 to 8, and more preferably 0 to 4, A represents a non-aromatic 5- or 6-membered carbon ring system, and R' and R'' are hydrogen, a C$_{1-8}$ alkyl or alkenyl group, phenyl or benzyl. Particularly advantageous cycloaliphatic radicals of the above type are those wherein the moiety

is an unsubstituted or mono- C$_{1-8}$ alkyl- or alkenyl-substituted cyclopentyl, cyclopentenyl, cyclohexyl, cyclohexenyl or cyclohexa-2,4-dienyl group. When R$_1$ is an aromatic hydrocarbon radical it will contain from 6 up to about 30 carbon atoms and may consist of a single ring or fused-ring system which can be unsubstituted or have one or more hydrocarbon groups substituted thereon. Especially useful aromatic radicals contain from 6 to 20 carbon atoms and correspond to the formula

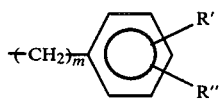

where m is an integer from 0 to 8, and more preferably 0 to 4, and R' and R'' are hydrogen, a C$_{1-8}$ alkyl or alkenyl group, phenyl or benzyl. Preferred aromatic radicals include phenyl, C$_{1-8}$ alkyl- or alkenyl-substituted phenyl, benzyl and C$_{1-8}$ alkyl- or alkenyl-substituted benzyl.

R$_1$ can also be an aliphatic, cycloaliphatic or aromatic moiety containing one or more oxygen, sulfur, nitrogen or halogen atoms, or a combination thereof. Such radicals can result from the substitution of a functional group on an aliphatic, cycloaliphatic or aromatic hydrocarbon radical, such as those previously described, or in the case of oxygen, sulfur and nitrogen, the atoms may be an integral part of a hydrocarbon chain or ring structure, i.e., R$_1$ is a heteroalkyl or heterocyclic radical. In the situation when the aliphatic, cycloaliphatic, or aromatic group is substituted with the functional group, the substituent may be halogen (fluorine, chlorine or bromine), nitro, amine, nitrile, thionitrile, isothionitrile, mercapto, hydroxy and the like. One or more of these groups may be substituted on the hydrocarbon chain or ring system which can contain up to 30 carbon atoms. R$_1$ can also be oxoalkyl or oxocycloalkyl radicals such as, for example:

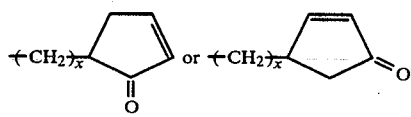

where x is 0 or 1 and the various ring positions may be substituted with a C$_{1-4}$ alkyl or alkenyl, phenyl, benzyl or phenoxy group.

When R$_1$ is a heteroalkyl or heterocyclic radical wherein the oxygen, sulfur or nitrogen forms an integral part of the hydrocarbon chain or hydrocarbon ring system, the radical will contain up to 30 carbon atoms. Especially useful heteroalkyl radicals contain from 2 to 20 carbon atoms and are derived from alkanolamines, such as ethanolamine; N,N-dialkylalkanolamines, such as N,N-dimethylethanolamine, and quaternized derivatives thereof; monoalkyl ethers of polyalkylene glycols, such as diethylene glycol, and higher poly(oxyalkylene) glycols; and the like. Especially useful heterocyclic radicals contain from 4 to 20 carbon atoms and have a 5- or 6-membered ring, or fused ring structure thereof. More than one heteroatom may be present in the ring and the heteroatoms need not be the same. Illustrative heterocyclic groups include:

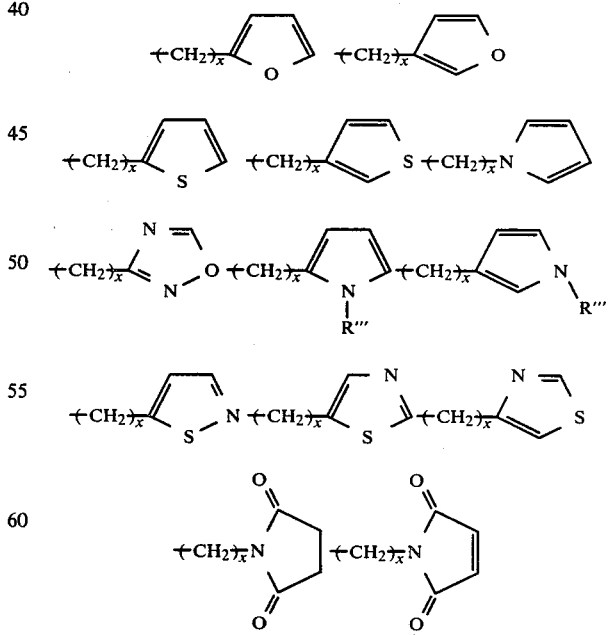

wherein x is 0 or 1, R''' is hydrogen or C$_{1-4}$ alkyl, and each of the available ring positions may be substituted with a C$_{1-4}$ alkyl or alkenyl, phenyl benzyl or phenoxy group and wherein hydrocarbon groups on adjacent positions may be joined to form a ring.

The radical Y, which is substituted on the same ring carbon atom as the carboxylate

moiety, is a nitrile —C≡N) group or an aryl radical having from 6 to 30 carbon atoms. The aryl moiety can be a single-ring or fused-ring system which can be unsubstituted or substituted with one or more hydrocarbon groups. Especially useful aryl groups from which Y is selected have from 6 to 20 carbon atoms and correspond to the formula

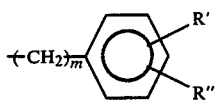

where m is an integer from 0 to 8, and more preferably 0 to 4, and R' and R" are hydrogen, a $C_{1-8}$ alkyl or alkenyl group, phenyl or benzyl. Preferred aromatic radicals from which Y is selected include phenyl, $C_{1-8}$ alkyl- or alkenyl-substituted phenyl, benzyl and $C_{1-8}$ alkyl- or alkenyl-substituted benzyl.

Especially advantageous 2-ethyl- and 2-vinylcyclopropane monocarboxylate compounds of this invention are those where Y is nitrile, phenyl or $C_{1-4}$ alkyl-substituted phenyl and $R_1$ is a heteroalkyl or heterocyclic group having from 3 to 20 carbon atoms and selected from the group:

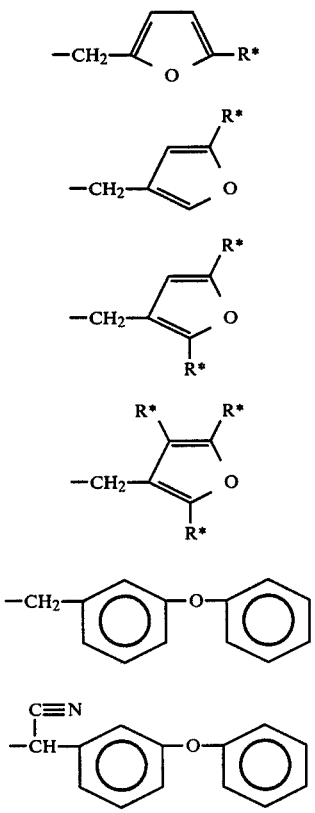

-continued

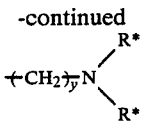

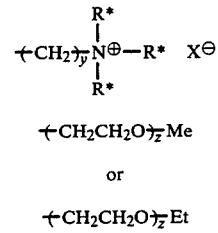

$+CH_2CH_2O)_z$Me or $+CH_2CH_2O)_z$Et where R* is a $C_{1-4}$ alkyl, $C_{1-4}$ alkenyl, $C_{1-4}$ hydroxyalkyl, phenyl or benzyl, Me is methyl, Et is ethyl, y is an integer from 2 to 6, z is an integer from 1 to 10 and X represents an anion such as halide, hydroxide, sulfate, nitrate, acetate, alkylsulfate, alkylphosphate, fluoroborate and the like.

To obtain the novel cyclopropane monocarboxylates of this invention the phase transfer process of U.S. Pat. No. 4,252,739, details of which are incorporated herein by reference, is utilized. This process involves reacting an alkylating agent and an activated methylene compound in the presence of an onium compound, an alkali metal compound and water. To obtain cyclopropane derivatives wherein Y is nitrile by the process of U.S. Pat. No. 4,252,739, an ester of α-cyanoacetic acid is reacted with an alkylating agent, typically a 1,4-dihalobutene-2. In a similar manner, esters of α-arylacetic acids are reacted with an alkylating agent such as 1,4-dichlorobutene-2 to obtain the 2-vinylcyclopropane derivatives wherein aryl and carboxylate groups are present in the 1-position of the ring.

Utilizing the above procedures, it is possible to directly obtain 2-vinylcyclopropane products having both a carboxylate moiety and a nitrile or aryl moiety substituted on the 1-position of the ring. These compounds are then conveniently reduced to obtain the corresponding 2-ethylcyclopropane products. Generally, the carboxylate obtained via the process of U.S. Pat. No. 4,252,739 will be a lower alkyl carboxylate but complex carboxylates can also be obtained directly by this process. It is more common practice, however, in order to obtain the more complex cyclopropane monocarboxylate products, i.e., compounds wherein the carboxylate is a bulky group or contains one or more functional groups, to first prepare the lower alkyl cyclopropane monocarboxylate and then to carry out a transalcoholysis reaction. Transalcoholysis of the lower alkyl cyclopropane monocarboxylates can be readily accomplished utilizing a wide variety of alcohols or mixtures of alcohols in accordance with established procedures.

In addition to transalcoholysis, a cyclopropane monocarboxylic acid can also be directly reacted with an alcohol or alcohol mixture employing conventional esterification procedures and suitable conditions to obtain the products of this invention. The cyclopropane monocarboxylates can also be obtained by reacting alkali metal salts of the aforementioned acids with suitable active halide compounds or acid halides can be reacted with the alcohol or corresponding alkali metal alkoxides.

Illustrative alcohols, or halides or alkoxides derived from these alcohols, which can be used to obtain the products of this invention in accordance with the above-mentioned procedures include but are not limited to the following:

2-methyl-1-pentanol
2-ethylhexanol
2-octanol
2,6-dimethyl-4-heptanol
dodecanol
hexadecanol
octadecanol
allyl alcohol
3-methyl-1-buten-3-ol
3-ethyl-1-buten-3-ol
3-methyl-3-penten-1-ol
1,4-pentadien-3-ol
5-cyclohexylidene-2-pentanol
2-methyl-2-hepten-6-ol
5,6-dimethyl-5-hepten-2-ol
6,10-dimethylundeca-5,9-dien-2-ol
3,7,11-trimethyldodeca-1,6,10-trien-3-ol
cyclopentanol
cyclohexanol
4-methylcyclohexanol
3-cyclobutyl-2-propen-1-ol
3-cyclopentyl-2-propen-1-ol
3-cyclohexyl-2-propen-1-ol
3-cycloheptyl-2-propen-1-ol
3-(4-chlorophenyl)-3-methyl-2-propen-1-ol
3-(4-methylphenyl)-3-methyl-2-propen-1-ol
3-(4-methylphenyl)-2-butyl-2-propen-1-ol
3-(4-methoxyphenyl)-1-methyl-2-propen-1-ol
3-(1-naphthyl)-2-propen-1-ol
3-(4-chloronaphth-1-yl)-2-propen-1-ol
3-(4-methylnaphth-1-yl)-2-propen-1-ol
benzyl alcohol
(3-phenoxyphenyl)carbinol
(3-thiophenyl)carbinol
2,4-dimethylbenzyl alcohol
2,4,6-trimethylbenzyl alcohol
4-allylbenzyl alcohol
2,6-dimethyl-4-allylbenzyl alcohol
4-(3'-methylbenzyl)benzyl alcohol
4-(2',4'-dimethylbenzyl)benzyl alcohol
2,6-dichlorobenzyl alcohol
benzhydrol
cinnamyl alcohol
p-methoxycinnamyl alcohol
2,4,5-trimethoxycinnamyl alcohol
p-benzylcinnamyl alcohol
p-benzyloxycinnamyl alcohol
m-bromocinnamyl alcohol
3-chloro-4-methoxycinnamyl alcohol
o-methoxycinnamyl alcohol
p-isopropoxycinnamyl alcohol
p-phenoxycinnamyl alcohol
p-methylcinnamyl alcohol
p-(methylphenethyl)cinnamyl alcohol
phenol
cresol
eugenol
isoeugenol
thymol
α-hydroxyacetophenone
cyclohexylphenol
t-butylphenol
nonylphenol
naphthol
2-phenoxyethanol
diethylene glycol monomethyl ether
triethylene glycol monoethyl ether
monoethanol amine
diethanol amine
triethanol amine
N-aminoethylethanol amine
2-(2-aminoethoxy)ethanol
3-Bis(2-hydroxyethyl)aminopropylamine
N-hydroxyethylethylene diamine
N-methyldiethanol amine
2-(2-(3-aminopropoxy)ethoxy)ethanol
2-methylaminoethanol
2-dimethylaminoethanol
2-diethylaminoethanol
N-2-hydroxyethylacetamide
2-anilinoethanol
2-N-ethylanilinoethanol
1-dimethylamino-2-propanol
1-(2-aminoethylamino)-2-propanol
4-(2'-thenyl)benzyl alcohol
furfuryl alcohol
(3-furyl)carbinol
thiofurfuryl alcohol
4-(2'furfuryl)benzyl alcohol
(5-benzyl-3-furyl)carbinol
2-(2',4'-dimethylbenzyl)-4-furfuryl alcohol
(5-benzyl-2-furyl)carbinol
(4-benzyl-5-methyl-2-furyl)carbinol
2-(4'-methylbenzyl)-5-furfuryl alcohol
(3-methyl-2-furyl)carbinol
(2-methyl-3-furyl)carbinol
(5-methyl-3-furyl)carbinol
(5-methyl-2-furyl)carbinol
(2,5-dimethyl-3-furyl)carbinol
(2,4,5-trimethyl-3-furyl)carbinol
(5-allyl-2-furyl)carbinol
(5-allyl-3-furyl)carbinol
5-hydroxymethyl-2,2'-difurylmethane
4-hydroxymethyl-2,2'-difurylmethane
(4,5-benzo-2-furyl)carbinol
(4,5-benzo-3-furyl)carbonol
5-phenoxy-2-thienyl alcohol
N-hydroxymethyl-3,4,5,6-tetrahydrophthalimide
N-hydroxymethyl phthalimide
N-hydroxymethyl thiophthalimide
N-hydroxymethyl-3,6-dihydrophthalimide
N-hydroxymethyl dimethylmaleimide
N-hydroxymethyl methylethylmaleimide
N-hydroxymethyl phenylmethylmaleimide
3-hydroxymethyl-5-benzyl-1,2,4-oxadiazole
1-benz-4-hydroxymethylpyrazole
3-methyl-2-cyclopenten-4-ol-1-one
2-allyl-3-methyl-2-cyclopenten-4-ol-1-one It will be evident to those skilled in the art that various geometric and stereo isomers of the cyclopropane monocarboxylate compounds, and mixtures and racemates thereof, will exist. For example, by varying the process and reaction conditions by which the compounds are prepared it is possible to impart preferential optical activity. Whereas the formula does not take into account isomeric forms, i.e. cis- and trans-configurations and dextro and levo forms, it is intended that the invention be construed to encompass all such forms and mixtures thereof.

The novel compounds of this invention are useful for a wide variety of applications, however, they are particularly useful as herbicides and insecticides. As employed herein, the term herbicide is used in its broadest sense to encompass any type of modification of plant growth including retardation of growth, defoliation, dessication, regulation, stimulation, dwarfing and, in some cases, killing the plant. In addition to treatment of established plants and emerging seedlings, the vinylcyclopropane monocarboxylate compounds of this invention can also be applied as a seed coating. The term insecticide is also used in the broad sense wherein it encompasses not only usage for the control of beetles, flies and mosquitos but also use for the control of spiders, lice, mites, ticks, nemotodes and other pests not classified as insects in the strict biological sense. Various isomeric forms will exhibit more activity than other isomers for certain of these applications.

The 2-vinyl- and 2-ethylcyclopropane monocarboxylate compounds of this invention may be utilized as such, they may be chemically modified by further reaction, or they may be utilized in combination with other known active compounds to enhance the overall insecticidal/herbicidal effectiveness. The ability to develop synergistic insecticidal and herbicidal formulations is generally well recognized in this art and the use of combinations including the products of this invention may provide a means of enhancing the overall activity and/or selectivity of the resulting formulation and/or making the compositions more cost effective. The cyclopropane monocarboxylates can be formulated with inert carriers or diluents or they may be prepared and utilized in the form of dusts, wettable powders, emulsions and the like.

Particularly useful cyclopropane products of this invention, in view of their ability to modify the growth of plants, are those compounds wherein R is vinyl or ethyl, Y is cyano or phenyl and $R_1$ is

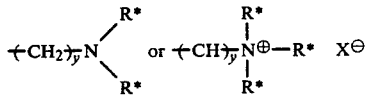

wherein R* is methyl, ethyl, hydroxymethyl or hydroxyethyl, X is chloride, bromide, hydroxide, sulfate or ethasulfate and y is an integer from 2 to 4.

Particularly useful vinylcyclopropane derivatives of this invention for insecticidal applications are those compounds wherein R is vinyl or ethyl, Y is cyano or phenyl and $R_1$ is 3-phenoxybenzyl, α-cyano-3-phenoxybenzyl, (5-benzyl-3-furyl)methyl and (2-benzyl-4-furyl)methyl.

The following examples more fully illustrate the preparation of the novel compounds of this invention and demonstrate the utility of these products. These examples are not intended to limit the scope of the invention since numerous variations and modifications are possible as will be evident to those skilled in the art to which the invention pertains. All parts and percentages provided in the examples are on a weight percent basis unless otherwise indicated.

EXAMPLE I

Ethyl 2-vinyl-1-cyanocyclopropane-1-carboxylate was prepared in accordance with the procedure of U.S. Pat. No. 4,252,739. For the reaction 750 ml benzene, 250 gms (2 moles) 1,4-dichlorobutene-2, 113 gms (1 mole) ethyl cyanoacetate and 3 gms tricaprylylmethylammonium chloride were charged to a reactor and heated to reflux with agitation. Potassium hydroxide (85%) pellets (132 gms; 2 moles) were then added to the stirred solution in small portions. A mild exotherm was observed with the addition of caustic and external cooling was provided as necessary to maintain mild reflux. When the KOH addition was complete the reaction was stirred at reflux for 5 hours while removing water by azeotropic distillation. The reaction mixture was then filtered and the benzene evaporated. Distillation under reduced pressure yielded ethyl 2-vinyl-1-cyanocyclopropane-1-carboxylate (B.p. 55° C. at 0.02 mm Hg, lit. 112° C. at 11 mm Hg.; $n_D^{25°}$ 1.4661, lit. $n_D^{24°}$ 1.4650).

EXAMPLE II

Utilizing the product prepared in Example I, a transalcoholysis was carried out with 3-phenoxybenzyl alcohol to obtain (3-phenoxy)benzyl 2-vinyl-1-cyanocyclopropane-1-carboxylate. A three-fold molar excess of the ethyl 2-vinyl-1-cyanocyclopropane-1-carboxylate was employed for the reaction. About 0.7 wt. percent calcium acetate, based on the total reactant charge, was used as the catalyst and a small amount of hydroquinone added as an oxidation and polymerization inhibitor. The reaction mixture was heated with agitation to 150° C. and about 4 wt. percent dibutyltin oxide charged. After 5 hours additional heating the reaction was terminated and the resulting product, containing about 35% of the desired (3-phenoxy)benzyl 2-vinyl-1-cyanocyclopropane-1-carboxylate, dissolved in ethyl ether, filtered to remove insoluble catalyst residue, washed with 5% aqueous sodium hydroxide and saturated sodium chloride solutions. After evaporation of the ethyl ether, the product was dissolved in toluene and separated from the unreacted starting materials using a Waters Preparatory Liquid Chromatograph 500A equipped with a gel permeation column and operated at a flow rate of 0.1 l/min. After two passes, 92+% pure (3-phenoxy)benzyl 2-vinyl-1-cyanocyclopropane-1-carboxylate was obtained and the structure of the product confirmed by mass spectroscopy and nuclear magnetic resonance spectroscopy.

Mass spectrum m/e 319(M+).

Nmr(CDCl₃)τ 2.35–3.10(9 aromatic H, mult); 3.90–4.70(3 vinyl H, mult.); 4.80(2H(φ—CH₂—),s.); 7.20–7.7(1H(2 cyclopropyl ring position), b. mult.); 8.05–8.63(2H(3 cyclopropyl ring position); mult.).

EXAMPLE III

In a manner similar to that described above, a transalcoholysis reaction was carried out using ethyl 2-vinyl-1-cyanocyclopropane-1-carboxylate and (5-benzyl-3-furyl)carbinol. The ratio of reactants, catalyst level, and reaction temperature employed were the same as indicated in Example II. (5-Benzyl-3-furyl)methyl 2-vinyl-1-cyanocyclopropane-1-carboxylate was obtained in 85.9% yield and purified by separation using the liquid chromatographic procedure. The structure of the purified (99.4%) product was confirmed by mass spectroscopy and nuclear magnetic resonance spectroscopy.

Mass spectrum m/e 307(M+).

Nmr (CDCl₃)τ 2.48(1H(2 furan position), b.s.); 2.61(5 phenyl H, s); 3.30(1H(4 furan position), b.s.); 4.00–4.82(3 vinyl H, mult.); 4.86(2H(φ—CH₂—O—),s); 5.99(2H(φ—CH₂—C , s); 7.16–7.7(1H(2 cyclo propyl ring position), b. mult.); 7.95–8.60(2H(3 cyclo propyl ring position), mult.).

Similar results are obtained when the ethyl 2-vinyl-1-cyanocyclopropane-1-carboxylate is first reduced using tosyl hydrazine and the resulting ethyl 2-ethyl-1- cyanocyclopropane-1-carboxylate employed for the transalcoholysis to prepare (5-benzyl-3-furyl)methyl 2-ethyl-1-cyanocyclopropane-1-carboxylate.

EXAMPLE IV 2-(N,N-dimethylamino)ethyl 2-vinyl-1-cyanocyclopropane-1-carboxylate was prepared by reacting essentially equimolar amounts of ethyl 2-vinyl-1-cyanocyclopropane-1-carboxylate and N,N-dimethylaminoethanol. For the reaction, a small amount of sodium metal (1.13 wt. %) was reacted with the N,N-dimethylaminoethanol prior to the addition of the ethyl 2-vinyl-1-cyanocyclopropane-1-carboxylate. The reaction mixture was stirred for 35 minutes after which time gas chromatographic analysis indicated the reaction to be 70% complete. After workup of the reaction mixture, the crude product was vacuum distilled to obtain the 2-(N,N-dimethylamino)ethyl 2-vinyl-1-cyanocyclopropane-1-carboxylate (B.p. 97° C. at 0.015 mm Hg). The infrared spectrum was consistent with the structure.

Nmr $(CDCl_3)\tau$ 3.97–4.85(3 vinyl H, mult.); 5.75(2H, tr.); 7.15–7.60(1H(2 ring position, hidden), mult); 7.37(2H, tr.); 7.74(6H,s); 7.85–8.55(2H(3 ring position), mult.).

EXAMPLE V

A quaternary salt of the 2-(N,N-dimethylamino)ethyl 2-vinyl-1-cyanocyclopropane-1-carboxylate (5.3 gms) prepared in Example IV was prepared by reaction with a molar excess of methyl chloride (21 gms). A pressure vessel was employed for the reaction and the reactants were allowed to stir at ambient temperature in 25 ml. absolute ethanol overnight. After venting the excess methyl chloride, the ethanol was removed under vacuum to obtain a viscous light yellow oil which was triturated with large amounts of ethyl ether. The resulting ether insoluble viscous oil was dried at room temperature under high vacuum for several days and the resulting 2-(N,N,N-trimethylamino)ethyl 2-vinyl-1-cyanocyclopropane-1-carboxylate chloride obtained as a light tan waxy deliquescent solid.

nmr $(CD_3OD)\tau$ 4.11–4.82(3 vinyl H, mult.); 5.05–5.55(2H, mult.); 5.80–6.25 (2H, mult.), 6.65(9H,s.); 6.9–7.61(1H,(2 ring position), mult.); 7.65–8.31 (2H(3 ring position), mult.).

When soybean leaves were exposed in a standard test for senescence, the 2-(N,N,N-trimethylamino)ethyl 2-vinyl-1-cyanocyclopropane-1-carboxylate chloride was found to promote senescence, as determined by measuring the chlorophyll content of the treated leaves.

EXAMPLE VI

Ethyl 2-vinyl-1-phenylcyclopropane-1-carboxylate was prepared in accordance with the procedure of U.S. Pat. No. 4,252,739. For the reaction 2600 ml. methylene chloride, 561 gms. potassium hydroxide (85%) and 5 mole percent tricaprylylmethylammonium chloride were charged to a reaction vessel and a mixture of ethyl phenylacetate (1.64 kilograms) and 1,4-dichlorobutene-2 (1.375 kilograms) slowly added over 1½ hours. An exotherm was observed and external cooling applied so that the temperature of the reaction mixture did not exceed 42° C. The reaction was then stirred at room temperature for 6 hours and an additional 561 gms. potassium hydroxide added in small portions over a one hour period. After an additional period of stirring and workup of the reaction mixture, the crude ethyl 2-vinyl-1-phenylcyclopropane-1-carboxylate was recovered and distilled under reduced pressure to obtain the final product (infrared spectrum consistent with structure; B.p. 113°–115° C. at 1.8 mm Hg.).

Mass spectrum m/e 216 (M+). Nmr $(CDCl_3)\tau$ 2.77(5H(phenyl), mult.); 3.76–5.36(3 vinyl H(cis, trans), mult.); 5.94(2H, q); 7.10–7.90(1H(2 ring position), mult.); 7.95–8.70(2H(3 ring position), mult.); 8.91(3H; tr.).

EXAMPLE VII

In a manner similar to that described in Example IV, 10.8 gms. ethyl 2-vinyl-1-phenylcyclopropane-1-carboxylate was added to about 50 gms. N,N-dimethylaminoethanol which had been previously reacted with 0.115 gms. sodium metal. The reaction mixture was then heated with stirring and ethanol formed as a result of the reaction removed under vacuum (20 mm Hg.). At the completion of the reaction, the mixture was poured into water, extracted with ether and after removal of the ether solvent, 98% pure 2-(N,N-dimethylamino)ethyl 2-vinyl-1-phenylcyclopropane-1-carboxylate obtained in 59% yield.

Nmr $(CDCl_3)\tau$ 2.72(5H(phenyl), mult.); 3.74–5.25(3 vinyl H(cis/trans), mult.); 5.86(2H, tr.); 7.58(2H, tr.); 7.10–7.90(1H(2 ring position), hidden mult.); 7.95–8.75(2H(3 ring position), mult.).

EXAMPLE VIII 2-(N,N-dimethylamino)ethyl 2vinyl-1-phenylcyclopropane-1-carboxylate was quaternized with methyl chloride in accordance with the procedure described in Example V, except that methanol was employed as the solvent medium. Upon removal of the solvent and after workup of the reaction product, 2-(N,N,N-trimethylamino)ethyl 2-vinyl-1-phenylcyclopropane-1-carboxylate chloride was obtained in 96% yield.

Nmr $(CD_3OD)\tau$ 2.65(5 phenyl H, mult.); 3.55–5.15(3 vinyl H, mult.); 5.5(2H($CO_2$—$CH_2$—), b. mult.); 6.80(2H(—$CH_2$—N$\oplus$, b. mult.); 7.01(9H(($CH_3$—$_3$—N$\oplus$), b.s.); 7.30–7.85(1H(2 ring position), mult.); 7.95–8.60(2H(3 ring position), mult.).

The quaternized compound was demonstrated to be an effective plant growth regulator for Chattanooga soybeans. The plants were grown at 26°–27° C. in commercial potting soil under "Duro-Lite Vita Lite" fluorescent light tubes. The lamps were on a 12-hour lighting cycle and were maintained 12" from the tops of the plants (adjusted for height every other day).

For the test, 14 day old Chattanooga soybean plants having two fully developed extended smooth leaves (3.5–5.0 cm across) and with trifoliate leaves still folded in a terminal bud, were uniformly drenched by spraying with an aqueous solution containing 1000 ppm of the quaternized product and 500 ppm wetting agent (polyoxyethylene sorbitan monolaurate). After spraying, the growth of the plants (uniformly watered so that the surface soil was never allowed to go dry) was recorded after four, five and six days. The length of the second internodes was measured and compared with the second internodes growth of unsprayed control plants. Percent growth retardation was then determined in accordance with the formula $$100 - \left[ \frac{\text{growth 2nd internode (mm)} - \text{treated plants}}{\text{growth 2nd internode (mm)} - \text{untreated plants}} \times 100 \right] =$$

-continued

Results were as follows:

|  | 4th day | 5th day | 6th day |
|---|---|---|---|
| % Retardation | 65 | 70 | 73 |

The effectiveness of the 2-(N,N,N-trimethylamino)ethyl 2-vinyl-1-phenylcyclopropane-1-carboxylate chloride is evident when the above results are compared with the results obtained using an aqueous solution containing 1000 ppm chlorocholine chloride, a commercially available product widely promoted as a growth regulator. Retardation of Chattanooga soybeans obtained with chlorocholine chloride was only 29% (4th day), 33% (5th day) and 29% (6th day).

EXAMPLE IX

Ethyl 2-vinyl-1-phenylcyclopropane-1-carboxylate was reduced to prepare ethyl 2-ethyl-1-phenylcyclopropane-1-carboxylate. For the reaction 13.47 gms ethyl 2-vinyl-1-phenylcyclopropane-1-carboxylate (0.062 mole) was combined with 23.06 gms tosyl hydrazine (0.124 mole) in 70 ml. diglyme and the reaction mixture heated with agitation at reflux for one hour. After cooling the reaction mixture was extracted with petroleum ether and, upon distillation, 8.4 gms (62% yield) ethyl 2-ethyl-1-phenylcyclopropane-1-carboxylate obtained. (B.p. 115°–117° C. at 2 mm Hg.).

Nmr (CDCl$_3$)$\tau$ 2.8(5 phenyl H, mult.); 5.96(2H(cis/trans), d.q.); 8.2–9.25(8H(ring H and CH$_3$CH$_2$—), mult); 8.98(3H,tr.).

EXAMPLE X

In accordance with the procedure described in Example IV, ethyl 2-ethyl-1-phenylcyclopropane-1-carboxylate was reacted with N,N-dimethylaminoethanol to obtain 2-(N,N-dimethylamino)ethyl 2-ethyl-1-phenylcyclopropane-1-carboxylate.

Nmr (CDCl$_3$)$\tau$ 2.73(5 phenyl H, mult.); 5.85(2H(CO$_2$CH$_2$—); tr.); 2.55(2H(—CH$_2$—N), tr.); 7.9(6H,s.); 8.13–9.25(8H(ring H and CH$_3$CH$_2$—); mult.).

The 2-(N,N-dimethylamino)ethyl 2-ethyl-1-phenylcyclopropane-1-carboxylate was then quaternized with methyl chloride in accordance with the usual procedure to obtain 2-(N,N,N-trimethylamino)ethyl 2-ethyl-1-phenylcyclopropane-1-carboxylate chloride in 94% yield.

Nmr (CD$_3$OD)$\tau$ 2.65(5 phenyl H, mult.); 5.5(2H(—CO$_2$CH$_2$—), b. mult.); 6.32 (2H(—CH$_2$—N$^\oplus$), mult.); 7.05(9H,s.); 8.1–9.25(8H(ring H and CH$_3$CH$_2$—), mult.).

The 2-(N,N,N-trimethylamino)ethyl 2-ethyl-1-phenylcyclopropane-1-carboxylate chloride, evaluated at a concentration of 1000 ppm in accordance with the procedure of Example VIII, produced 59, 63 and 75% growth retardation of Chattanooga soybeans after 4, 5 and 6 days, respectively.

We claim:
1. A method of modifying soybean growth comprising applying to said soybean plants an effective growth modifying amount of a compound of the formula

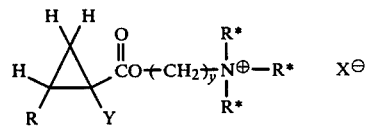

where R is ethyl or vinyl, Y is nitrile or phenyl, R* is methyl, ethyl, hydroxymethyl or hydroxyethyl, X is chloride, bromide, hydroxide, sulfate, or ethasulfate, and y is an integer from 2 to 4.

2. The method of claim 1 wherein the growth modifying compound is 2-(N,N,N-trimethylamino)ethyl 2-vinyl-1-cyanocyclopropane-1-carboxylate chloride.

3. The method of claim 1 wherein the growth modifying compound is 2-(N,N,N-trimethylamino)ethyl 2-vinyl-1-phenylcyclopropane-1-carboxylate chloride.

4. The method of claim 1 wherein the growth modifying compound is 2-(N,N,N-trimethylamino)ethyl 2-ethyl-1-phenylcyclopropane-1-carboxylate chloride.

* * * * *